(12) United States Patent
Jacoby et al.

(10) Patent No.: US 7,279,605 B2
(45) Date of Patent: Oct. 9, 2007

(54) SYNTHESIS OF CYCLOPENTENONES

(75) Inventors: Denis Jacoby, Nyon (CH); Fabrice Keller, Satigny (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/737,510

(22) Filed: Apr. 19, 2007

(65) Prior Publication Data

US 2007/0197833 A1    Aug. 23, 2007

Related U.S. Application Data

(63) Continuation of application No. PCT/IB2005/053717, filed on Nov. 11, 2005.

(30) Foreign Application Priority Data

Nov. 11, 2004  (WO) ................. PCT/IB2004/003719
Nov. 18, 2004  (WO) ................. PCT/IB2004/003854

(51) Int. Cl.
*C07C 45/72*   (2006.01)

(52) U.S. Cl. ...................................... 568/343; 568/345

(58) Field of Classification Search ..................... None
See application file for complete search history.

(56) References Cited

U.S. PATENT DOCUMENTS

| | | | |
|---|---|---|---|
| 6,686,498 B2 * | 2/2004 | Jacoby | 560/174 |
| 6,838,575 B2 * | 1/2005 | Jacoby | 560/200 |
| 7,091,151 B2 * | 8/2006 | Jacoby | 502/171 |

OTHER PUBLICATIONS

Tsuyoshi Yuki et al., "Direct Synthesis of Polysubstituted Cyclopentenones from Ketones and Aldehydes Catalyzed by Zirconium Compounds", Journal of Organic Chemistry, Vo91. 58, No. 16, pp. 4497-4499 (1993).

\* cited by examiner

*Primary Examiner*—Sikarl A. Witherspoon
(74) *Attorney, Agent, or Firm*—Winston & Strawn LLP

(57) ABSTRACT

The invention relates to a process for the preparation, in a single step, of substituted 2-cyclopenten-1-ones by reacting a substituted enone with an aldehyde in the presence of a catalytic system. The catalytic system consists of a metal complex, such as a $Ti(Cl)_3(alkoxy)$, and a co-ingredient, such as a carboxylic acid anhydride or an anhydrous salt.

8 Claims, No Drawings

SYNTHESIS OF CYCLOPENTENONES

CROSS-REFERENCE TO RELATED APPLICATIONS

This application is a continuation of International application PCT/IB2005/053717 filed Nov. 11, 2005, the entire content of which is expressly incorporated herein by reference thereto.

TECHNICAL FIELD

The present invention relates to the field of organic synthesis and more precisely to a single step process for the synthesis of a cyclopentenone derivative of formula

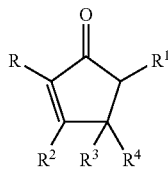

(I)

as defined further below.

BACKGROUND

Ishii et al., in J. Org. Chem., 1993, 58, 4497, reports the synthesis of cyclopentenone derivatives from the reaction of a ketone with two equivalents of an aldehyde or by the reaction of an enone with an aldehyde, which is catalyzed by Zirconium chloride derivatives such as $ZrOCl_2$ or $ZrCl_4$, the oxide being described as the best catalyst.

However, the procedure reported by Ishii requires severe conditions such as high temperature (between 130 and 200° C., the upper part of the range giving the best results, see Table I). Such severe conditions may result in poor yields (for example 17% when all the ring substituents are methyl groups, reaction carried out at 200° C.). These conditions are not of high industrial interest since are not environmentally friendly, and require much energy and produce high amounts of wastes.

SUMMARY OF THE INVENTION

The present invention now relates about the use of a specific catalytic system for the preparation of cyclopentenones by reacting together a suitable enone and a suitable aldehyde. The catalytic system comprise a metal salt of formula $M(OR^5)_{4-n}X_n$, as defined further below, and a co-ingredient, as defined further below (e.g. an anhydrous salt or a carboxylic anhydride).

DETAILED DESCRIPTION OF THE PREFERRED EMBODIMENTS

In order to overcome all or part of the problems aforementioned, the present invention relates to a process for the preparation of cyclopentenone derivatives that can be carried out with soft conditions and accessory can result in high yields.

One of the embodiments of the invention is a process for the preparation of a compound of formula

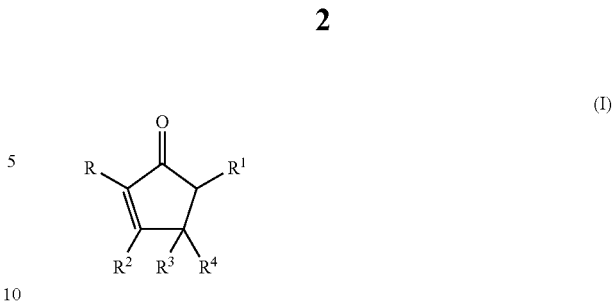

(I)

wherein R represents a $C_{1-8}$ alkyl or alkenyl group optionally substituted or a $C_{5-6}$ aromatic, optionally substituted; and $R^1$, $R^2$, $R^3$ and $R^4$ represent, simultaneously or independently, a hydrogen atom, a $C_{1-8}$ alkyl or alkenyl group optionally substituted or a $C_{5-6}$ aromatic group, optionally substituted.

This process comprises the reaction between an enone of formula

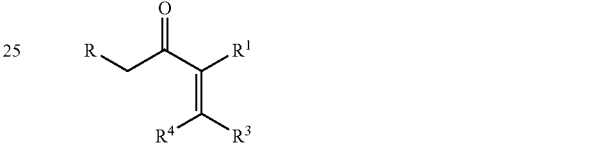

(II)

wherein R, $R^1$, $R^3$ and $R^4$ have the same meaning as in formula (I);

with an aldehyde of formula

(III)

wherein $R^2$ has the same meaning as in formula (I); and the reaction between the enone (II) and the aldehyde (III) being performed in the presence of a catalytic system comprising:

i) at least one metal complex of formula

$$M(OR^5)_{4-n}X_n \quad (IV)$$

wherein M is Ti(IV) or Zr(IV), $R^5$ represents a $C_{1-6}$ linear or branched alkyl group, X represents a halide and n represents an integer from 1 to 3; and ii) at least one co-ingredient selected from the group consisting of a) an alkyl or aromatic carboxylic acid anhydride containing 2 to 10 carbon atoms;

b) an anhydrous sulfate, chloride or bromide of a metal cation selected from the group consisting of $Li^+$, $Na^+$, $K^+$, $Cs^+$, $Mg^{2+}$, $Ni^{2+}$, $Ca^{2+}$, $Zn^{2+}$, $Fe^{3+}$ and $Al^{3+}$;

c) an insoluble inorganic material capable to form a clathrate with water; and d) a $C_4$-$C_{15}$ orthoester, $BF_3$, N-methyl-N-trimethylsilyl-trifluoroacetamide, 1-trimethylsilylimidazole and ClSi$(R^6)_3$, $R^6$ representing a $C_{1-5}$ alkyl group.

Possible optional substituents of the groups R, $R^1$, $R^2$, $R^3$ and $R^4$ are groups which do not affect the reactivity of the enone (II) or of the aldehyde (III). Examples of the optional substituents, when the R, $R^1$, $R^2$, $R^3$ and $R^4$ groups represent alkyl or alkenyl group, include one or two methyl, ethyl, methoxy or ethoxy groups. Examples of the optional substituents, when the R, $R^1$, $R^2$, $R^3$ and $R^4$ groups represent an aromatic group, include one or two methyl, ethyl, methoxy, ethoxy or nitro groups.

According to a particular embodiment of the invention, R represents a $C_{1-8}$ alkyl or alkenyl group or $C_{5-6}$ aromatic group optionally substituted. Alternatively, $R^1$, $R^2$, $R^3$ and $R^4$ represent, simultaneously or independently, a hydrogen atom, a $C_{1-8}$ alkyl or alkenyl group or a $C_{5-6}$ aromatic group optionally substituted.

In particular according to the embodiment, R represents a $C_{1-8}$ alkyl or alkenyl group, and $R^1$, $R^2$, $R^3$ and $R^4$ represent, simultaneously or independently, a hydrogen atom, a $C_{1-8}$ alkyl or alkenyl group.

In another embodiment of the invention, there is obtained an enone of formula (I), from the corresponding compounds (II) and (III), wherein R represents a methyl, ethyl or pentyl group or a phenyl group optionally substituted. Alternatively, or simultaneously, $R^1$, $R^2$, $R^3$ and $R^4$ represent, simultaneously or independently, a hydrogen atom, a methyl, ethyl or pentyl group or a phenyl group optionally substituted.

In particular according to the embodiment, R represents a methyl, ethyl or pentyl group, and $R^1$, $R^2$, $R^3$ and $R^4$ represent, simultaneously or independently, a hydrogen atom, a methyl, ethyl or pentyl group.

According to any one of the above-mentioned embodiments, $R^4$ represents a hydrogen atom. In particular, the R, $R^1$, $R^2$ or $R^3$ represents, simultaneously or independently, a methyl, ethyl or phenyl group optionally substituted, or just a methyl or ethyl group, while $R^4$ represents a hydrogen atom.

According to a further embodiment of the invention, the ketone (II) can be obtained in situ by reacting together a ketone (V) and a ketone or aldehyde (VI), in the presence of the same catalytic system of the invention's process, according to Scheme 1.

Scheme 1

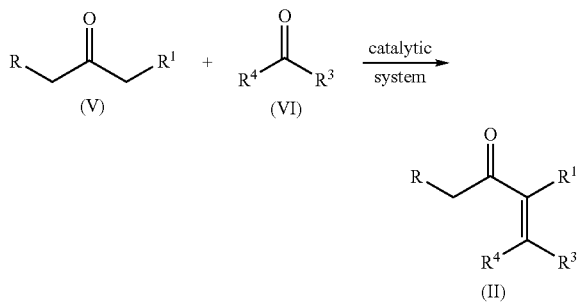

wherein R, $R^1$, $R^3$ and $R^4$ have the same meaning as indicated above.

Therefore the present invention concerns also a process further comprising the step mentioned above.

Particular examples of suitable ketones (II), (V) or (VI) are diethyl ketone, dibenzyl ketone, methyl phenyl ketone, ethyl phenyl ketone or hexyl methyl ketone.

Particular examples of suitable aldehydes (III) or (VI) are acetaldehyde, formaldehyde, propanaldehyde or benzaldehyde.

According to a further embodiment of the invention, the process comprises a first step wherein are reacted together a diethyl ketone and acetaldehyde to obtain a ketone of formula (II), which is subsequently reacted with acetaldehyde.

According to an embodiment of the present invention the molar ratio between the enone (II) and the aldehyde (III) is comprised between 1.1/1 and 1/6, more preferably between 1/1 and 1/5 and even more preferably between 1/1.1 and 1/5. Furthermore, the molar ratio between the ketone (V) and the compound (VI) is comprised between 1/1 and 1/8, more preferably between 1/2.5 and 1/6 and even more preferably between 1/3 and 1/5.

As mentioned above, the process of the invention is carried out in the presence of a catalytic system, which consists of a metal complex and of a co-ingredient. The metal complex is used in substoechiometric, or catalytic amounts, relative to the starting aldehyde or ketone.

The metal complex has a general formula:

$$M(OR^5)_{4-n}X_n \quad \text{(IV)}$$

wherein M, n, $R^5$ and X have the meaning given above. According to a particular embodiment of the invention, M represents Ti(IV), $R^5$ represents a linear or branched $C_{3-4}$ alkyl group, X represents a Cl atom and the index n represents 2 or 3.

The use of a mixture of metal complexes of formula (IV) is also convenient, especially if the catalyst is synthesized in situ, and without purification, prior to its use in the process.

According to a particular embodiment of the invention, the co-ingredient of the catalytic system is selected from the group consisting of an alkyl or aromatic carboxylic acid anhydride containing 4 to 8 carbon atoms, $BF_3$, $ClSi(R^6)_3$, $R^6$ representing a $C_{1-5}$ alkyl group, and an anhydrous sulfate, chloride or bromide of a metal cation selected from the group consisting of $Na^+$, $K^+$, $Mg^{2+}$, $Ca^{2+}$, $Zn^{2+}$, $Fe^{3+}$.

Preferably, the co-ingredient is selected from the group consisting of acetic, propionic or butyric anhydride, $BF_3$, $ClSi(R^6)_3$, $R^6$ representing a methyl or ethyl group. the anhydrous $Na_2SO_4$ or $K_2SO_4$ and an anhydrous chloride or bromide of $Mg^{2+}$, $Fe^{3+}$ or $Zn^{2+}$.

The use of a mixture of two or three co-ingredients is also possible.

The metal complex can be added to the reaction medium in a large range of concentrations. As non-limiting examples, one can cite catalyst concentrations ranging from 0.01 to 0.20 molar equivalents, relative to the molar amount of the starting ketone (II) or (V). Preferably, the metal complex concentration will be comprised between 0.01 and 0.10 molar equivalents. It goes without saying that the optimum concentration of catalyst will depend on the nature of the latter and on the desired reaction time.

The co-ingredient can be added to the reaction medium in a large range of concentrations. As non-limiting examples, one can cite salt concentrations ranging from 0.05 to 1.2 molar equivalents, relative to the number of moles of the starting ketone (II) or (V). Preferably, the salt concentration will be comprised between 0.10 and 0.60 molar equivalent. Yet, in another preferred embodiment, the salt concentration will be comprised between 0.20 and 0.50 molar equivalents. It goes without saying that the optimum concentration of the additional agent will depend on the nature of the latter.

The process of the invention can be carried out in the presence or absence of solvent, but in any case it is advantageously performed in anhydrous conditions, wherein by "anhydrous" it is meant here a solvent which has a content in water below 1% by weight, preferably below 0.1%. When a solvent is required, it is possible to use a pure solvent or a mixture of solvents. The solvent must be chemically compatible with the reaction conditions, i.e. not interfere with the reaction, and not deactivate the catalyst, e.g. a weak or non-coordinating solvent. Preferred solvents for the process of the invention have a boiling point higher than 60° C. and are selected from the group consisting of ethers, esters, aromatic solvents, and linear or branched or cyclic hydrocarbons. More preferably, the solvent is an ester such as butyl acetate.

Furthermore, the solvent can be the starting ketone (II) or (V) or the starting aldehyde (III) or (VI).

The temperature at which the process of the invention can be carried out is comprised between 60° C. and 140° C., preferably between 70° C. and 100 or 110° C. Of course a person skilled in the art is also able to select the reaction temperature as a function of the melting and boiling point of the starting and final products and/or the possible solvent.

EXAMPLES

The invention will now be described in further detail by way of the following examples, the temperatures are indicated in degrees centigrade (° C.); the NMR spectral data were recorded with a 360 MHz machine in $CDCl_3$, the chemical displacement δ are indicated in ppm with respect to the TMS as standard, the coupling constant J are expressed in Hz and all the abbreviations have the usual meaning in the art.

Example 1

Synthesis of 2,3,4,5-tetramethyl-2-cyclopenten-1-one a) Preparation of the Metal Catalyst Solution A catalytic solution containing the $TiCl_3(O^iPr)$ complex is obtained according to the procedure described in E. V. Vedejs et al., J. Org. Chem., (1988), 53, 1593 but using the $TiCl_4$ and the $Ti(O^iPr)_4$ complexes as starting materials. The quantities were modified in order to obtain catalytic solution with a concentration of 1.3 mmole of metal per gram of catalytic solution.

All the resulting solutions were used without further manipulation.

b) Preparation of 2,3,4,5-tetramethyl-2-cyclopenten-1-one

In a bottom round flask equipped with a mechanical stirrer, a dropping funnel and a reflux condenser was loaded 2000 g (23.2 mol) of the starting ketone with 75% w/w of butylacetate as the solvent, 0.35 molar equivalents of anhydrous magnesium chloride and the aforementioned titanium catalytic solution containing 0.06 molar equivalents of the trichloropropoxytitanium complex. The resulting suspension was stirred vigorously and allowed to heat to 90° C. Then 2 molar equivalents of the acetaldehyde were added dropwise over 3 h at 90° C. The reaction was continued for an additional hour and cooled to 40° C. The reaction mixture was hydrolysed with a 10% aqueous acetic acid solution and neutralised with a 20% aqueous potassium carbonate solution.

The resulting organic phase was directly fractionated into a laboratory Sulzer packed column, to afford the title compound, as a mixture of isomers trans:cis=85:15, in 27% yield (B.p.=70-80° C. at P=8 mbar) and the enone (II) (i.e. 4-methyl-4-hexen-3-one) in 31% yield (B.p.=45-65° C. at P=8 mbar).

$^1$H-NMR (isomer trans): 1.15 (d 3H); 1.19 (d 3H); 1.68 (s 3H); 1.88 (m 1H); 1.98 (s 3H); 2.25 (m 1H).

$^{13}$C-NMR (isomer trans): 8.5; 14.6; 15.1; 17.7; 46.2; 48.4; 134.5; 171.6; 211.0.

Example 2

Synthesis of 3,4-diethyl-2,5-dimethyl-2-cyclopenten-1-one

In a bottom round flask equipped with a mechanical stirrer, a dropping funnel and a reflux condenser were loaded 265 g (3.08 mol) of the diethyl ketone with 252 g of butylacetate as the solvent, 0.36 molar equivalents of anhydrous magnesium chloride and the aforementioned titanium catalytic solution containing 0.053 molar equivalents of the trichloropropoxytitanium complex. The resulting suspension was stirred vigorously and allowed to heat to 85° C. Then 2.1 molar equivalents of propionaldehyde were added dropwise over 2 h at 85° C. The reaction was continued for an additional hour and cooled to 40° C. The reaction mixture was hydrolyzed with a 10% aqueous acetic acid solution (500 g), decanted and washed with a 10% aqueous acetic acid solution (200 g) and 50 g of NaCl. The organic phase was then washed twice with a 20% aqueous potassium carbonate solution.

After drying over $Na_2SO4$, the solvent was evaporated. The crude product (419.6 g), was distilled through a Vigreux column and then fractionated through a Fischer column, to afford the title compound in 17% yield (B.p.=58° C. at P=3 mbar) and the enone (II) (i.e. 4-methyl-4-hepten-3-one) in 32% yield (B.p.=84° C. at P=43 mbar).

MS: 166 (76); 151 (37); 138 (100); 137 (94); 109 (72); 67 (54); 41 (30)

$^1$H-NMR: 2.52 (1H; m); 2.29 (2H; m); 2.01(1H; dq; 2.5 Hz; 8 Hz); 1.90-1.80 (1H;m);1.69 (3H; br s); 1.34-1.22 (1H; m); 1.17 (3H; d; J=6 Hz); 1.10 (3H; d; J=7 Hz);0.94 (3H; d; J=8 Hz).

$^{13}$C-NMR: 211.8 (s); 175.9 (s); 134.4 (s); 50.5 (d); 45.2 (d); 25.2(t); 21.8 (t); 16.9 (q),11.8 (q); 11.4 (q); 8.0 (q).

Example 3

Synthesis of Various Compounds of Formula (I)

General Procedure for Cyclopentenone Process

In a bottom round flask equipped with a mechanical stirrer, a dropping funnel and a reflux condenser was loaded 1 molar equivalents of the starting ketone (see further below) neat or with 75% w/w of butylacetate as the solvent, 0.35 molar equivalents of anhydrous magnesium chloride and the aforementioned titanium catalytic solution containing 0.05 molar equivalents of the trichloropropoxytitanium complex. The resulting suspension was stirred vigorously and allowed to heat to 90-100° C. Then the aldehyde of formula (III) (see further below) was dropped over 3 hours at 90-100° C. The reaction was continued an additional hour at 90-100° C. and cooled to 40° C. The reaction mixture was hydrolyzed with a 10% hydrochloric acid solution and neutralized with a 20% potassium carbonate solution.

The resulting organic phase was directly fractionated into a laboratory Sulzer packed column. The results are summarized herein below.

Experiment A)

Starting ketone: 4-methyl-4-hexen-3-one
Starting aldehyde: benzaldehyde (1.2 molar equivalents)
Products:

4-phenyl-2,3,5-trimethyl-2-cyclopenten-1-one +3-phenyl-2,4,5-trimethyl-2-cyclopenten-1-one (20/80)
yield: 25% (based on used starting ketone)
yield: 45% (based on converted starting ketone)
Analysis for the major product (3-phenyl-2,4,5-trimethyl-2-cyclopenten-1-one):
$^1$H-NMR: 1.08 (d, 3H); 1.25 (d, 3H); 1.88 (s, 3H); 2.05 (m, 1H); 2.85 (m, 1H); 7.3-7.5 (m, 5H).
$^{13}$C-NMR: 9.5; 15.5; 19; 45; 48.5; 127-129 (6C); 135; 170.5; 211.

Experiment B)
Starting ketone: 4-methyl-4-hexen-3-one
Starting aldehyde: 10-undecenal (0.9 molar equivalents)
Products:
4-(9-decenyl)-2,3,5-trimethyl-2-cyclopenten-1-one +3-(9-decenyl)-2,4,5-trimethyl-2-cyclopenten-1-one (33/66)
yield: 36% (based on used starting ketone)
yield: 72% (based on converted starting ketone)
Analysis of the mixture obtained:
$^1$H-NMR: 1.15 (d); 1.17 (d); 1.25-1.40 (m); 1.70 (s); 1.90 (m); 2.0 (s); 2.05 (m); 2.35 (m); 2.50 (m); 4.95 (m, 2H); 5.80 (m, 1H).
$^{13}$C-NMR: 8; 15; 17; 18; 27; 28-30; 33; 34; 44; 47; 49; 52; 114; 135; 135.5; 139; 171; 175.5; 211.

Experiment C)
Starting ketone: 5-ethyl-4-methyl-4-hepten-3-one
Starting aldehyde: acetaldehyde (1.2 molar equivalents)
Products:
4,4-diethyl-2,3,5-trimethyl-2-cyclopenten-1-one
yield: 40% (based on used starting ketone)
yield: 58% (based on converted starting ketone)
Analysis of the product:
$^1$H-NMR: 0.45 (t, 3H); 0.78 (t, 3H); 1.08 (d, 3H); 1.35-1.70 (m, 4H); 1.70 (s, 3H); 1.85 (s, 3H); 2.20 (q, 1H).
$^{13}$C-NMR: 7.95; 8.75; 9.60; 10.10; 12.30; 27.55; 29.95; 46.40; 51.85; 136.3; 171.1; 210.3.

Experiment D)
Starting ketone: Diethylketone
Starting aldehyde: Benzaldehyde (3.0 molar equivalents)
Products:
3,4-diphenyl-2,5-dimethyl-2-cyclopenten-1-one cis/trans: 15/85
yield: 32% (based on used starting ketone)
yield of ketone (II): 24% (based on used starting ketone)
Analysis of the product:
Trans isomer
$^1$H-NMR: 1.34 (d, J=7.17, 3H); 2.02 (s, 3H); 2.40 (dq, $J_1$=7.17, $J_2$=2.56, 1H); 3.97 (sb, 1H); 7.0-7.3 (m 10H)
$^{13}$C-NMR: 10.1; 15.3; 51.25; 56.33; 126-129 (10 CH); 135.2 ; 136.7; 142 ; 167; 210.9
Cis isomer
$^1$H-NMR: 0.75 (d, J=7.68, 3H); 2.08 (s, 3H); 2.92 (m, 1H); 4.6 (d, J=6.14, 1H); 7.0-7.3 (m, 10H)
$^{13}$C-NMR: 9.8; 12.3; 45.5; 52.5; 126-129 (10 CH); 135.7; 136.9; 139.2; 166.3; 211.4

Experiment E)
Starting ketone: 1-3 diphenylacetone
Starting aldehyde: acetaldehyde (3.0 molar equivalents)
Products:
3,4-dimethyl-2,5-diphenyl-2-cyclopenten-1-one cis/trans: 15/85
yield: 48% (based on used starting ketone)
yield of ketone (II): 36% (based on used starting ketone)
Analysis of the product:
Trans isomer
$^1$H-NMR: 1.35 (d, J=6.65, 3H); 2.17 (s, 3H); 2.87 (dq, $J_1$=6.65, $J_2$=3.07, 1H); 3.23 (d, J=3.07, 1H); 7.1-7.4 (m, 10H)
$^{13}$C-NMR: 15.9; 18.1; 47.7; 60.7; 126-129 (10 CH); 131.8 ; 138.9; 139.5 ; 174; 205.
Cis isomer
$^1$H-NMR: 0.8 (d, J=7.17, 3H); 2.15 (s, 3H); 3.15 (m, 1H); 3.95 (d, J=7.17, 1H); 7.1-7.4 (m, 10H).
$^{13}$C-NMR: 16.1; 16.3; 42.8; 56.7; 126-129 (11 CH); 137.7; 139.7; 174.7; 206.5

What is claimed is:
1. A process for the preparation of a compound of formula

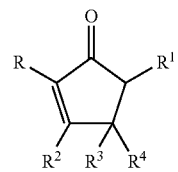

(I)

wherein R represents a $C_{1-8}$ alkyl or alkenyl group optionally substituted or a $C_{5-6}$ aromatic, optionally substituted; and
$R^1$, $R^2$, $R^3$ and $R^4$ represent, simultaneously or independently, a hydrogen atom, a $C_{1-8}$ alkyl or alkenyl group optionally substituted or a $C_{5-6}$ aromatic group, optionally substituted;
the process comprising the reaction between an enone of formula

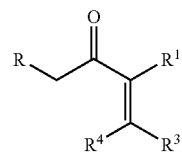

(II)

wherein R, $R^1$, $R^3$ and $R^4$ have the same meaning as in formula (I);
with an aldehyde of formula

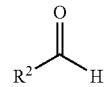

(III)

wherein $R^2$ has the same meaning as in formula (I); and
the reaction between the enone (II) and the aldehyde (III) being performed in the presence of a catalytic system comprising:
i) at least one metal complex of formula $$M(OR^5)_{4-n}X_n \quad (IV)$$

wherein M is Ti(IV) or Zr(IV), $R^5$ represents a $C_{1-6}$ linear or branched alkyl group, X represents a halide and n represents an integer from 1 to 3; and ii) at least one co-ingredient selected from the group consisting of
  a) an alkyl or aromatic carboxylic acid anhydride containing 2 to 10 carbon atoms;
  b) an anhydrous sulfate, chloride or bromide of a metal cation selected from the group consisting of $Li^+$, $Na^+$, $K^+$, $Cs^+$, $Mg^{2+}$, $Ni^{2+}$, $Ca^{2+}$, $Zn^{2+}$, $Fe^{3+}$ and $Al^{3+}$;
  c) an insoluble inorganic material capable to form a chlatrate with water; and
  d) a $C_4$-$C_{15}$ orthoester, $BF_3$, N-methyl-N-trimethylsilyl-trifluoroacetamide, 1-trimethylsilylimidazole and $ClSi(R^6)_3$, $R^6$ representing a $C_{1-5}$ alkyl group.

2. A process according to claim 1, wherein R represents a $C_{1-8}$ alkyl or alkenyl group; and $R^1$, $R^2$, $R^3$ and $R^4$ represent, simultaneously or independently, a hydrogen atom, a $C_{1-8}$ alkyl or alkenyl group.

3. A process according to claim 1, wherein R represents a methyl, ethyl or pentyl group or a phenyl group optionally substituted.

4. A process according to claim 1, wherein $R^1$, $R^2$, $R^3$ and $R^4$ represent, simultaneously or independently, a hydrogen atom, a methyl, ethyl or pentyl group or a phenyl group optionally substituted.

5. A process according to claim 1, wherein R, $R^1$, $R^2$ or $R^3$ represents, simultaneously or independently, a methyl, ethyl or phenyl group optionally substituted, and $R^4$ represents a hydrogen atom.

6. A process according to claim 1, wherein the enone (II) is obtained in situ by reacting together a ketone of formula

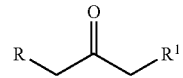

with an aldehyde or ketone of formula

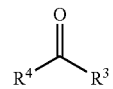

wherein R, $R^1$, $R^3$ and $R^4$ have the same meaning as in claim 1;
in the presence of a catalytic system as defined in claim 1.

7. A process according to claim 1, wherein M represents Ti(IV), $R^5$ represents a linear or branched $C_{3-4}$ alkyl group, X represents a Cl atom and the index n represents 2 or 3.

8. A process according to claim 5, wherein the co-ingredient of the catalytic system is selected from the group consisting of an alkyl or aromatic carboxylic acid anhydride containing 4 to 8 carbon atoms, $BF_3$, $ClSi(R^6)_3$, $R^6$ representing a $C_{1-5}$ alkyl group, and an anhydrous sulfate, chloride or bromide of a metal cation selected from the group consisting of $Na^+$, $K^+$, $Mg^{2+}$, $Ca^{2+}$, $Zn^{2+}$, $Fe^{3+}$.

* * * * *